United States Patent
Fox et al.

(10) Patent No.: US 6,273,858 B1
(45) Date of Patent: Aug. 14, 2001

(54) SYSTEMS AND METHODS FOR PROVIDING RADIATION THERAPY AND CATHETER GUIDES

(75) Inventors: Timothy H. Fox, Atlanta; Ian R. Crocker, Stone Mountain, both of GA (US)

(73) Assignee: Emory University, Atlanta, GA (US)

(*) Notice: Subject to any disclaimer, the term of this patent is extended or adjusted under 35 U.S.C. 154(b) by 0 days.

(21) Appl. No.: 09/603,563

(22) Filed: Jun. 26, 2000

Related U.S. Application Data

(62) Division of application No. 09/021,198, filed on Feb. 10, 1998, now Pat. No. 6,083,167.

(51) Int. Cl.$^7$ .................................................. A61B 8/14
(52) U.S. Cl. .................................... 600/466; 600/467
(58) Field of Search .............................. 600/437, 459, 600/462, 463

(56) References Cited

U.S. PATENT DOCUMENTS

| | | |
|---|---|---|
| 3,987,281 | 10/1976 | Hodes . |
| 4,796,637 | 1/1989 | Mascuch et al. . |

(List continued on next page.)

OTHER PUBLICATIONS

Nath, et al., "Dosimetry of interstitial brachytherapy sources: Recommendations of the AAPM Radiation Therapy Committee Task Group No. 43," *Med. Phys.* 22(2):209–234 (Feb. 1995).

Novoste™ 1996 Annual Report.

"Hyal Receives First U.S. Patent Allowance for Prevention of Restensois," *Canada News Wire,* (Dec. 1996).

Fox, et al., "Calculated Dose Distributions of Beta–Particle Sources Used for Intravascular Brachytherapy," American Society of Therapeutic Radiology and Oncology (ASTRO) Annual Conference, Orlando, Florida (Oct. 19–23, 1997).

(List continued on next page.)

*Primary Examiner*—Marvin M. Lateef
*Assistant Examiner*—Ali M. Imam
(74) *Attorney, Agent, or Firm*—John S. Pratt; Geoff L. Sutcliffe; Kilpatrick Stockton LLP

(57) ABSTRACT

A system and method for the prevention of restenosis uses a source of radiation to treat the blood vessel. An intravascular ultrasound system acquires precise two-dimensional images of a treatment volume. The intravascular ultrasound system enables medical personnel to obtain precise measurements of the distance between the radiation source and the lesion. Whereas conventional techniques for measuring this distance relied upon external imaging devices, the intra-vascular ultrasound system obtains in-vivo images allowing precise measurements to be taken at the point at which the radiation will be delivered. A computer-based treatment planner acquires the images from the imaging system and reconstructs a three-dimensional image of the treatment volume. From a dose prescription, the treatment planner calculates and optimizes the dose and also registers the dose with images of the treatment volume. A voice recognition unit allows medical personnel to provide voice commands for operating the system. The treatment planner and imaging system may be placed within the cath lab and enables the treatment plan to be dynamically changed based on patient specific information and avoids the need for the patient to travel to a different location for the imaging. A catheter guide is formed with a set of markers which produce image artifacts. A first pair of markers are used to determine a reference axis so that the precise orientation of the imaging transducer may be deduced and a third marker is used to permit clinicians to determine the precise location of the transducer along the length of the catheter guide.

19 Claims, 11 Drawing Sheets

U.S. PATENT DOCUMENTS

| | | |
|---|---|---|
| 4,802,487 | 2/1989 | Martin et al. . |
| 4,911,170 | 3/1990 | Thomas, III et al. . |
| 4,917,097 | 4/1990 | Proudian et al. . |
| 4,951,686 | 8/1990 | Herlitze . |
| 5,027,818 | 7/1991 | Bova et al. . |
| 5,054,492 * | 10/1991 | Scribner et al. ............ 600/462 |
| 5,209,730 | 5/1993 | Sullivan . |
| 5,259,837 * | 11/1993 | Von Wormer ............ 600/437 |
| 5,327,885 | 7/1994 | Griffith . |
| 5,339,812 | 8/1994 | Hardy et al. . |
| 5,345,938 | 9/1994 | Nishiki et al. . |
| 5,357,550 | 10/1994 | Asahina et al. . |
| 5,361,768 | 11/1994 | Webler et al. . |
| 5,391,139 | 2/1995 | Edmundson . |
| 5,398,690 | 3/1995 | Batten et al. . |
| 5,409,000 | 4/1995 | Imran . |
| 5,429,617 | 7/1995 | Hammersmark et al. . |
| 5,456,680 | 10/1995 | Taylor et al. . |
| 5,485,846 | 1/1996 | Webler et al. . |
| 5,497,776 | 3/1996 | Yamazaki et al. . |
| 5,514,128 | 5/1996 | Hillsman et al. . |
| 5,592,942 | 1/1997 | Webler et al. . |
| 5,596,990 | 1/1997 | Yock et al. . |
| 5,614,506 | 3/1997 | Falk et al. . |
| 5,618,266 | 4/1997 | Liprie . |
| 5,643,171 | 7/1997 | Bradshaw et al. . |
| 5,643,251 | 7/1997 | Hillsman et al. . |
| 5,651,364 | 7/1997 | Yock . |
| 5,660,180 | 8/1997 | Malinowski et al. . |
| 5,669,878 | 9/1997 | Dickinson et al. . |
| 5,676,151 | 10/1997 | Yock . |
| 5,682,897 | 11/1997 | Pomeranz . |
| 5,683,345 | 11/1997 | Waksman et al. . |
| 5,701,900 | 12/1997 | Shehada et al. . |
| 5,707,332 | 1/1998 | Weinberger . |
| 5,727,553 | 3/1998 | Saad . |
| 5,859,891 | 1/1999 | Hibbard . |
| 5,879,305 * | 3/1999 | Yock et al. ............ 600/462 |
| 5,882,291 | 3/1999 | Bradshaw et al. . |
| 6,004,269 * | 12/1999 | Crowley et al. ............ 600/439 |

OTHER PUBLICATIONS

Moran, John F., "Management of Restenosis: The Challange for Angioplasty in the 1990's," *Midwest Cardiovascular Institute, Good Samaritan Hospital, Viewpoint* (Winter 1996).

Mintz, Gary S., et al., "Intravascular Ultrasound Predictors of Restenosis After Percutaneous Transcather Coronary Revascularization" *J. Am. Coll. Cardiol.* 27:1678–1687 (1996).

Soares, et al., "Calibration and characterization of beta–particle sources for intravascular brachytherapy," *Med. Phys.*, 25(3):339–346 (1998).

EndoSonics, "Oracle® Imaging System IntraCoronary Ultrasound Imaging," pp. 1–3 (website date Dec. 10, 1997).

EndoSonics, "In–Vision™ The Future in IntraCoronary Ultrasound Now . . . " pp. 1–6 (website date Dec. 10, 1997).

EndoSonics, "EndoSonics Announces Software for 3–Dimensional Display of Intravascular Ultrasound Images," pp. 1–2 (website date Dec. 10, 1997).

EndSonics, "Solid–State Intracoronary Ultrasound: A Technology Whose Time Has Come," pp. 1–3 (website date Dec. 10, 1997).

* cited by examiner

SYSTEMS AND METHODS FOR PROVIDING RADIATION THERAPY AND CATHETER GUIDES

This application is a divisional of U.S. Ser. No. 09/021,198 entitled "Systems and Methods for Providing Radiation Therapy and Catheter Guides" filed on Feb. 10, 1998 by Timothy H. Fox and Ian R. Crocker, now U.S. Pat. No. 6,083,167.

FIELD OF THE INVENTION

The present invention relates generally to systems and methods devices for providing radiation therapy and, more particularly, to systems and methods for providing radiation therapy for the prevention of restenosis. According to another aspect, the invention generally relates to catheter guides for enabling clinicians to determine location or orientation of catheters.

BACKGROUND OF THE INVENTION

A leading cause of death in the western world is atherosclerosis. More than thirteen million people in the United States have been diagnosed with this disease with a large number of patients having arteries or veins that have become narrowed and need to be enlarged. Angioplasty, a common technique to enlarge an artery or vein, is an interventional radiologic technique in which a narrowed artery or vein is enlarged with the use of a balloon angioplasty catheter.

To perform an angioplasty, an angiogram is used to obtain a precise image of the narrowed artery or vein. A catheter is inserted into a blood vessel and is guided to the site of the narrowing with an X-ray monitor. A contrast medium is injected through the catheter and a series of X-ray images are obtained to outline the blood vessel. The images obtained from the X-ray are used to identify and measure the abnormal narrowing of the blood vessel. The initial catheter used for diagnostic purposes is then removed and a catheter having an inflatable balloon around its shaft is inserted. The balloon is inflated in the narrowed portion of the vessel to widen the artery or vein. In some cases, a metallic stent is placed within the blood vessel in order to widen the blood vessel.

Although the initial success rate is high, the long-term success rate of angioplasty is unfortunately rather low and a subsequent procedure is often necessary. It has been estimated that nearly 25–45% of the 450,000 coronary angioplasties done in the United States each year fail within the first few months of the operation. Restenosis is defined to be the reclosing of the artery or vein to less than 50% of its original size. Because of restenosis, an additional angioplasty or another procedure, such as bypass surgery, is necessary to reopen the blood vessel. The need for subsequent procedures has a traumatic effect on the patient and on those concerned about the patient's health and additionally greatly increases medical costs. In fact, the cost to the health care system in the United States for subsequent procedures has been estimated to be 2 billion dollars annually.

The problems associated with restenosis are not limited only with an angioplasty procedure but also occur with other coronary revascularization procedures. Restenosis, for instance, is also associated with rotoblator, atherectomy catheters, hot and cold laser catheters, transluminal extraction catheters, and ultrasonic ablation. The magnitude of the problem caused by restenosis is therefore quite extensive.

Restenosis is difficult to prevent since its cause is not completely understood. Restenosis, however, is believed to be primarily caused by intimal hyperplasia and negative remodeling, and, to a lesser extent, elastic recoil. Angioplasty, as well as other revascularization techniques, expose the medial smooth muscle of the blood vessel to circulating mitogenic factors when the artery is dilated. As a result of platelet degranulation, growth factors are released which induce mitogenesis and promote proliferation of cells. Vascular smooth muscle cells consequently migrate into the intima, where they synthesize collagen and elastin, which comprise the bulk of the restenotic lesion.

One approach to combating restenosis is through drug therapy. Some agents tested in restenosis trials include antiplatelet agents, anticoagulants, thromboxane antagonists, prostanoids, calcium channel blockers, ACE inhibitors, antiproliferative growth factor inhibitors, lipid lowering agents, vitamins and antioxidants, and corticosteroids and non-steriodial A. Another agent that has been used to prevent restenosis is hyaluaronic acid. The use of hyaluaronic acid is shown and described in U.S. Pat. No. 5,614,506 to Falk et al., the disclosure of which is incorporated herein. The use of agents to block restenosis has generally been met with failure or at most limited success. The drug trials involving these agents have been fraught with problems such as incomplete angiographic follow-up, variable definitions of restenosis, small sample sizes, and varying drug dosage.

Another approach used to combat is the use of a stent. A polymer stent, for instance, is placed within the treated blood vessel and delivers medicine to the damaged blood vessel. The polymer stent need not be removed since it naturally dissolves after the blood vessel has been repaired. Stents have produced promising results in that they appear to significantly reduce the rate of restenosis by approximately 10%. Studies of stent usage, however, have revealed undesirable side effects, such as an increased incidence of bleeding complications associated with stent implantation. Stents unfortunately are unable to completely eliminate restenosis and a need exists for a treatment method that even further reduces the rate of restenosis.

An emerging and promising treatment for coronary restenosis is intracoronary radiation therapy (ICRT). In general, intracoronary radiation therapy delivers radiation to a damaged area of the blood vessel to prevent restenosis. A delivery catheter allows a radiation source to be delivered to the angioplasty site where it remains for a number of minutes before being withdrawn. The radiation source may be a line or "train" of several miniature cylindrical sealed sources containing a radioactive material, such as Sr-90, Ir-192, I-125, or Re-186. Rather than a train of radiation sources, other irradiation delivery techniques include radioactive seeds or pellets, radioactive wires, intravascular x-ray sources, and liquid-filled balloons emitting particulate or electromagnetic radiation. A radiation source never comes in contact with the patient's tissue or blood and a transfer device shields the radiation from health care workers during its handling. One advantage of intracoronary radiation therapy is that it typically adds less than ten minutes to the total procedure time and is easily incorporated within the cath lab. An example of an intracoronary radiation therapy is shown and described in U.S. Pat. No. 5,683,345 to Waksman et al., the disclosure of which is incorporated herein.

Trials of intracoronary radiation therapy have produced promising results. In one trial, for instance, one-half of a group of patients received gamma radiation and the other half received placebo treatment while all of the patients in this trial had a coronary stent. The preliminary results of the study showed that the treated group had a restenosis rate of 17%, compared with a restenosis rate of 54% in the non-treated group. Intracoronary radiation therapy has also shown to be preferable over the use of a stent. For instance, coronary stents typically produce a late loss index of 25 to 30%, meaning that on average 70 to 75% of the initial improvement in lumen diameter achieved by angioplasty was still present six months later. In contrast, a study involving intracoronary radiation therapy reduced the late loss index to only 5%, meaning that on average 95% of the initial improvement in lumen diameter was still present six months later. When only those patients receiving a higher dosage of radiation were evaluated, the late loss index dropped to zero. This study therefore suggests that with proper dosing level, additional devices or therapies should not be necessary.

The success of the intracoronary radiation therapy trials also point to shortcomings of the therapy. As discussed above, the success of intracoronary radiation therapy depends upon the proper dosage level with dosimetry measured in the sub-millimeter range being essential to optimally prescribing and delivering the radiation to the lesion. Proper dosing is difficult to achieve since it is dependent, among other things, upon the distance between the source of radiation and the lesion and upon the exposure time. Presently, X-ray imaging is used to determine the size of the vessel. The calculation or measurement of the dose-rate at a certain distance from the source is next made to determine the dwell-time required to deliver a certain dose given the vessel size.

Achieving the proper dosing is difficult with conventional methods. Since the imaging techniques used to estimate distances produce two-dimensional images, an accurate distance between the radiation source and the lesion cannot easily be obtained due to possible undetectable differences in location along the third dimension. As a result of errors in estimating the distance, the lesion may not be exposed to the radiation for the correct period of time. The proper dose, moreover, depends upon the lumen size and the wall thickness of the blood vessel, both of which cannot be accurately measured through conventional imaging techniques. Because of inaccuracies in measuring the distance between the source and lesion, the lumen size, and the wall thickness, optimal results with intracoronary radiation therapy are difficult to achieve. Intracoronary radiation therapy therefore cannot be successfully performed in a consistent manner.

Furthermore, conventional radiation treatment planning is less than optimal for this irradiation. A typical radiation treatment plan involves data entry and digitization of anatomical regions and images. The time needed to determine the distance and the dwell-time would delay the immediate treatment of a patient and may be detrimental to the patient's health. A conventional radiation treatment planning system would prevent medical personnel from adjusting or altering their treatment plan before treatment which may be necessary due to unforeseen circumstances discovered during the revascularization technique, such as the lumen size, wall thickness, and other patient specific information. A need therefore exists for a radiation treatment planning system which addresses the shortcomings of conventional treatment planning.

Another difficulty encountered with conventional treatment methods is identifying the position of a catheter within the blood vessel. This difficulty relates both to the position of the catheter along the length of a blood vessel and also pertains to the rotational position of the catheter. In other words, with conventional techniques, it is difficult and at times impossible to know the precise position and orientation of a catheter within the patient's body. This problem of locating a catheter is problematic not only in the treatment of restenosis but is encountered in virtually all uses of a catheter. Furthermore, this problem occurs when assessing the magnitude of a patient's illness, when arriving at a treatment plan, during the treatment of the patient, and also during the verification of a particular treatment.

To illustrate the problem in locating a catheter with conventional techniques, consider a situation in which a patient has a lesion along a particular length of an artery and intracoronary radiation is to be used to treat the lesion. The position of the catheter is first approximately placed at a desired location within the patient and this desired location may be verified with fluoroscopy. U.S. Pat. No. 5,054,492 to Scribner et al., the disclosure of which is incorporated herein by reference, provides one example of how a marker may be placed on a catheter guide and viewed through fluoroscopy in order to verity the location of catheter. The catheter is placed at the approximate position of the distal end of the lesion through the use of an automatic pull-back mechanism. The precise location of the catheter cannot be obtained but the approximate location of the catheter is estimated by calculating the speed of the catheter with the time that it has been moved in order to arrive at the traveled distance. With the catheter at the approximate location of a distal end of the lesion, the lesion is exposed to the radiation source and the dwell-time and dwell-positions of the radiation source or sources is again controlled with the automatic pull-back mechanism by estimating distance from the catheter speed and time of travel. Because of the inherent inaccuracies in indirectly estimating the position of a catheter through the parameters of speed and time, a need exists for systems and methods that allow the position of a catheter to determined more accurately.

Another limitation in catheter technology is that the rotational orientation of the catheter is typically not monitored. As a result, even though a lesion may only be located along one segment of an artery and not along an entire circumference of the lumen wall, the radiation is delivered in all directions in order to ensure that the lesion receives the radiation. Because conventional techniques do not allow the radiation to be directed only to the lesion, the radiation is often needlessly exposed to healthy portions of the artery. A need therefore exists for systems and methods that allow radiation to be focused to only certain segments of the arterial wall.

Even if radiation should be applied to the entire surface of an artery, it is difficult if not impossible to deliver a uniform dose of radiation. In delivering the radiation, assumptions are made that the artery is linear and that the radiation is distributed in a uniform manner. These assumptions, however, are often incorrect due to various factors, such as a curve in the artery which may result in a higher concentration of radiation being delivered at surfaces of the artery closest to the turn and lower concentrations being delivered at arterial surfaces farther away from the turn. Because of difficulty in controlling the rotational orientation of a catheter, conventional techniques are unable to optimally deliver a dose to a lesion.

One obstacle to the optimal delivery of a dose is the inability to detect the rotational position of the catheter. With many catheters, it is impossible to ascertain the rotational position of the catheter within the patient. U.S. Pat. No. 5,054,492 to Scribner et al. and U.S. Pat. No. 5,596,990 to Yock et al., the disclosures of which are both incorporated herein by reference, are directed to this problem but offer incomplete solutions. Scribner and Yock disclose catheter guides having a marker that serves as a landmark. With Scribner, an ultrasonic catheter is equipped with an ultrasonically opaque marker which appears as an artifact on resultant images taken with the transducer. The catheter also has a fluoroscopic marker that is used to identify the rotational position of the catheter from which the orientation of the ultrasonic marker may be deduced. Yock relates to a catheter having an ultrasonic catheter having a marker that is placed at a predetermined orientation and an image of the marker is produced.

Although Scribner and Yock offer improvements in that they provide some reference to estimate orientation, these references provide an initial orientation but do not allow the precise orientation of the catheter to be determined at all locations along a treatment volume. Since the catheter may twist or turn as it is being moved along the treatment volume, the initial indication of orientation provided by the marker may lead clinicians to an incorrect assumption about the orientation of the catheter. Scribner and Yock, moreover, do not assist clinicians in their estimate of the catheter's position along the length of a treatment volume. A need therefore still exists for devices and methods that enable the precise determination of a catheter's location and orientation.

SUMMARY OF THE INVENTION

The present invention addresses the problems described above by providing systems and methods that may substantially reduce the rate of restenosis. An imaging system acquires in-vivo images within a blood vessel or other area to be treated with radiation at each position along the length of the treatment volume and these images are passed along to a treatment planner. The imaging system includes an automatic pull back mechanism for moving an ultrasonic transducer along the length of a treatment volume. Alternatively, the system may incorporate stereotactic localization in order to track the position and orientation of the transducer. The imaging system acquires images at the same position of the radiation source whereby accurate distances from the radiation source to a lesion or other tissue to be treated may be obtained.

The treatment planner receives the images from the imaging system, either through a frame grabber or more preferably through a network interface that delivers the digital image data. The treatment planner assembles the plurality of transverse two-dimensional images and reconstructs a three-dimensional image of the treatment volume with each pixel having a unique x and y set of coordinates and each image being assigned a unique z coordinate. The treatment planner also has a dose calculator for determining a dose from a dose prescription and an optimizer for deriving an optimal dose for a particular treatment volume. A dose and image registration unit within the treatment planner overlays the dose upon the treatment volume and displays this information to medical personnel on a display, video recorder, or on some other output device. The treatment planner outputs the treatment plan and provides this plan to medical personnel, such as through a printer or monitor.

With a method according to the invention, an ultrasonic transducer is inserted within a treatment volume and is pulled back until it reaches a distal end of a treatment volume. An automatic pull back mechanism within the imaging system is then initiated and images are acquired at each position along the length of the blood vessel or other tissue to be treated. With each image acquired, the treatment planner assigns each pixel an x and y coordinate and also assigns each image plane a z coordinate. If optimization is enabled, the dose is set based on segmented anatomy and the dwell-time and positions of the radiation source are optimized. If optimization is not enabled, then the prescription point and source position are set. The dose is calculated and the dose is registered with the treatment volume images. After the dose has been registered with the images, both quantitative and qualitative plan evaluations are performed. If the plan is unacceptable, then the treatment planner performs another iteration of optimization or alters the values for the prescription point and source position.

A catheter guide, according to another aspect of the invention, allows for the precise tracking of a catheter's location and orientation. The catheter guide includes a first set of markers that produce image artifacts allowing clinicians to accurately arrive at a reference axis and a second set of markers allowing clinicians to accurately determine the position of a catheter along a length of a treatment volume. In one example of the invention, the first set of marker comprise straight lines formed parallel to each other along the length of the catheter guide and the second set of markers comprise straight lines that intersect the first set of markers. With the reference axis provided by the first set of markers, the orientation of the catheter and thus the orientation of resultant images can be accurately determined. Through knowledge of the orientation and position of the catheter, radiation can be focused or directed to only desired surfaces of an arterial wall along select portions of the artery. Other advantages and uses for the catheter guide will become apparent from the detailed description below.

Accordingly, it is an object of the present invention to provide systems and methods that substantially reduces the rate of restenosis.

It is a further object of the present invention to provide systems and methods that may be used to accurately and consistently deliver radiation.

It is yet another object of the present invention to provide systems and methods for allowing treatment plans to be iteratively changed, such as in response to unforeseen patient-specific information.

It is yet a further object of the present invention to provide systems and methods for the prevention of restenosis that reduce delays in the determination of a treatment plan.

It is a further object of this invention to allow determination of the rotational and longitudinal correlation of a catheter.

Other objects, features, and advantages of the present invention will become apparent with respect to the remainder of this document.

BRIEF DESCRIPTION OF THE DRAWINGS

The accompanying drawings, which are incorporated in and form a part of the specification, illustrate preferred embodiments of the present invention and, together with the description, disclose the principles of the invention. In the drawings.

DETAILED DESCRIPTION

Figure 1:
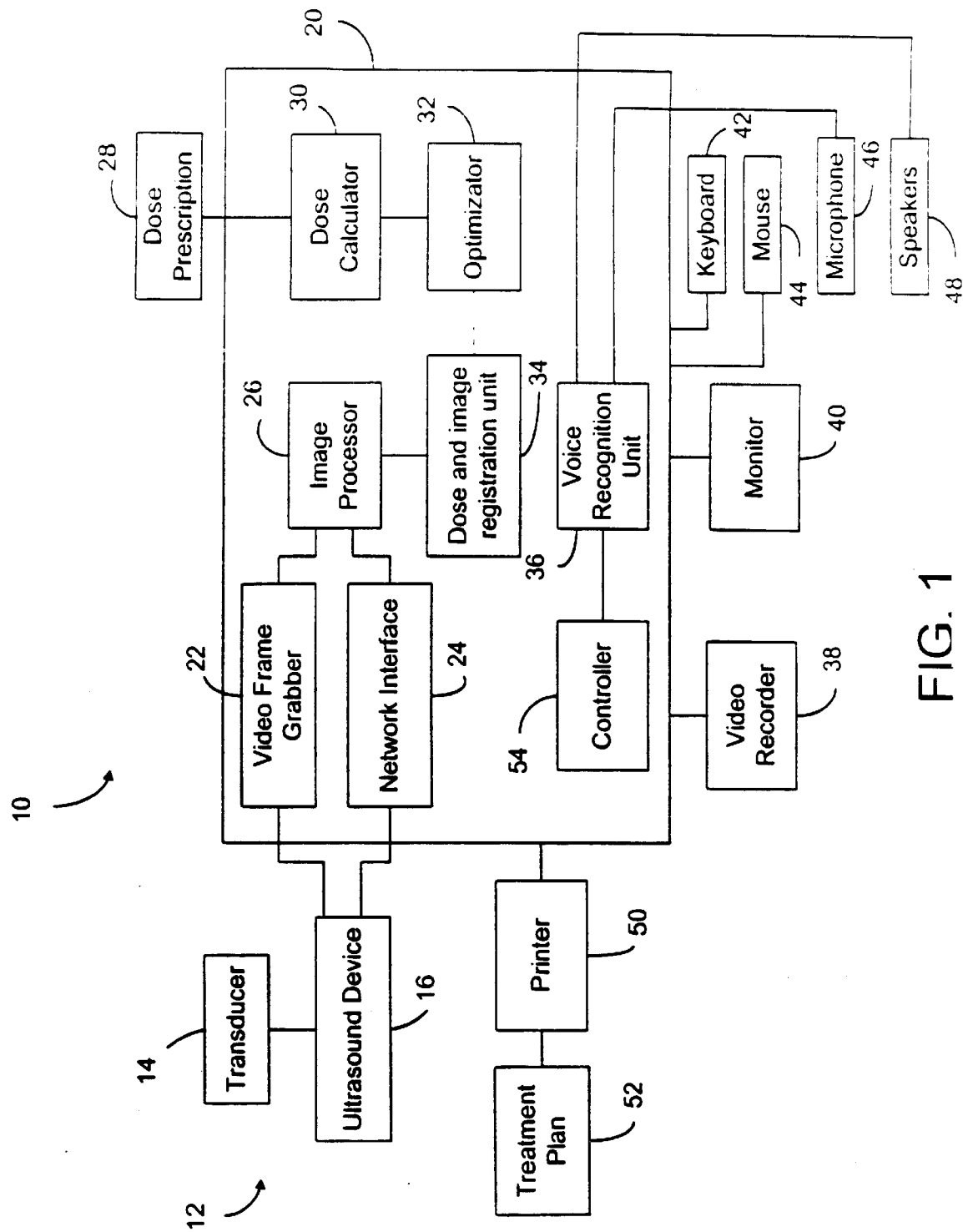
FIG. 1 is a block diagram of a system according to a preferred embodiment of the invention.

Reference will now be made in detail to preferred embodiments of the invention, non-limiting examples of which are illustrated in the accompanying drawings. With reference to FIG. 1, a radiation treatment planning and verification system 10 according to a preferred embodiment of the invention includes a treatment planner 20 and an imaging system 12. The imaging system 12 is an in-vivo imaging system in that it generates images of a treatment volume from within the blood vessel or other area to be treated. The imaging system 12 is preferably an ultrasonic system having a transducer 14 and an ultrasound device 16 for controlling operations of the transducer 14. The preferred imaging system 12 is commonly referred to as an intravascular ultrasound (IVUS) system. One exemplary IVUS system that may be used is the ORACLE® InVision™ intravascular ultrasound imaging system manufactured by Endosonics Corporation of Rancho Cordovo, Calif., although other IVUS systems may be used.

An ultrasonic imaging catheter comprises a catheter body having a distal end and a proximal end. The ultrasonic imaging transducer 14 is located within the distal end and is arranged to produce an image in an image plane which is generally normal to the axial direction of the catheter. An imaging coordinate system is established to define the image planes relative to the position of the imaging transducer 14 within the catheter. The x-y plane coordinates are associated with the axial direction of the catheter on the ultrasound image plane and the z coordinate is used for the value of the image plane, which is normal to the axial direction of the catheter.

The IVUS 12 is capable of imaging the vessel lumen, the thickness of the arterial wall, breaks or dissections in the arterial wall following intervention, and distribution of plaque and calcium deposits in the vessel wall. The ultrasound device 16 of the system 12 includes, in one embodiment, an automated motorized pull-back mechanism for moving the transducer 14 along the length of the treatment volume The IVUS system 12 produces transverse images of sections of the arterial lumen and wall as the transducer 14 is moved along the length of the treatment volume.

The treatment planner 20 acquires the images from the IVUS system 12 and combines the transverse images to generate a three-dimensional image of the treatment volume. The treatment planner 20 may include a video frame grabber 22 for acquiring each transverse image and for supplying each frame to an image processor 26. Instead of or in addition to the video frame grabber 22, the treatment planner 20 preferably includes a network interface 24 for transferring the digital image data produced by the IVUS system 12 directly to the image processor 26. With the network interface 24, the image processor 26 has available the precise digital data from which it can reconstruct the images of the treatment volume and can also perform other processing of the digital image data The image processor 26, as alluded to above, acquires data from the IVUS system 12 and produces three-dimensional images of the treatment volume, which are supplied to a dose and image registration unit 34.

In order to determine the proper dose, a dose prescription 28 must first be supplied to the treatment planner 20. The dose prescription 28 indicates the type and magnitude of radiation. The dose prescription 28, for instance, may specify radioactive seeds or pellets, a radioactive wire, an intravascular x-ray source, a liquid-filled balloon emitting radiation, or other techniques for delivering radiation to the treatment volume. The dose prescription 28, moreover, may specify different levels of radiation at different locations in the image data set and may be supplied to the treatment planner 20 in any suitable manner, such as through manual keying of the data with a keyboard 42, through the use of a mouse 44, or through use of a microphone 46, speakers 48, and voice recognition unit 36.

The dose prescription 28 is received by a dose calculator 30 within the treatment planner 20. In general, the dose calculator 30 determines the dose from the prescribed source of radiation at each point within the treatment volume. The dose calculator 30 provides the calculated dose information to an optimizer 32 which, in general, provides the optimal dose for a particular treatment volume.

The dose calculator 30 may use various methods for determining the absorbed radiation dose to human tissue. These methods include but are not limited to Monte Carlo, semi-empirical methods, and experimentally measured data from a radiation detector with adequate spatial resolution.

The dose and image registration unit 34 receives the dose information from the optimizer 32 and the image information from the image processor 26 and registers the dose with the images. The dose and image registration unit 34 indicates the dose deposited throughout the target volume and displays this information on a monitor 40. The dose and image registered information from the unit 34 may also be supplied to a video recorder 38 and to other units not shown.

The dose and image registration unit 34 visualizes the dose deposited throughout the treatment volume by using both qualitative and quantitative dose evaluation methods. A qualitative method allows the clinician to subjectively judge a two-dimensional (2-D) or three-dimensional (3-D) picture of isodose surfaces superimposed with imaging data. Joining points of common dose in a calculated dose distribution creates isodose distributions. The visualization of dose with respect to the treatment volume can be shown not only on the axial images, but also on reformatted saggital and coronal images. Surface or volume rendering techniques can be used for displaying the 3-D views of the isodose distribution with the treatment volume or imaging data. In addition to qualitative tools for judging the merit of a computed dose distribution, quantitative tools such as dose volume histograms (DVH) or dose surface histograms (DSH) and minimum/maximum dose for structure contours are methods used to further evaluate these dose distributions. The use of DVHs summarizes the 3-D dose distribution data into a graphical representation of lesion and other structures of interest, such as the lumen wall, media, and adventia. Also, besides using DVHs on structure contours, the concept can also be applied to treatment volumes and isodose levels. The use of minimum/maximum dose to the lesion and other structures of interest gives a quantitative assessment of the dose range. Also, the average dose and median dose to a structure contour can be computed. Other ways of registering and evaluating the dose on images of the treatment volume will be apparent to those skilled in the art.

After the treatment planner 20 has completed its processing, a finalized treatment plan 52 is generated with a printer 50. The treatment plan 52 is then used by medical personnel in delivering the proper dose to the treatment volume. The treatment plan, for instance, specifies the dwell-time of the radiation source for each position along the length of a blood vessel or other treatment volume.

The treatment planner 20 further includes a controller 54 for controlling the operations of the various elements within the treatment planner 20. The controller 54, for instance, receives commands or data supplied through the voice recognition unit 36 or through other devices, such as the keyboard 42 or mouse 44. The controller 54 also controls operations of the printer 50, video recorder 38, and monitor 40. The data and commands received at the controller 54 are used in the operations of the other elements of the planner 20, such as the image processor 26, dose calculator 30, optimizer 32, and dose and image registration unit 34.

The treatment planner 20 preferably comprises a computer having at least a 200 MHz processor. The treatment planner 20 includes a sound card which is preferably a Sound Blaster 32 bit sound card manufactured by Creative Labs of Melpitas, Calif. The video frame grabber 22 is a ComputerEyes frame grabber manufactured by Digital Vision of Dedham, Mass., and the network interface is a Ethernet twisted pair/thinnet interface card manufactured by 3COM of Santa Clara, Calif. The planner 20 runs on Windows 95 operating system and preferably comprises at least 32 MB of RAM and at least a 6 GB hard drive.

Figure 2A:
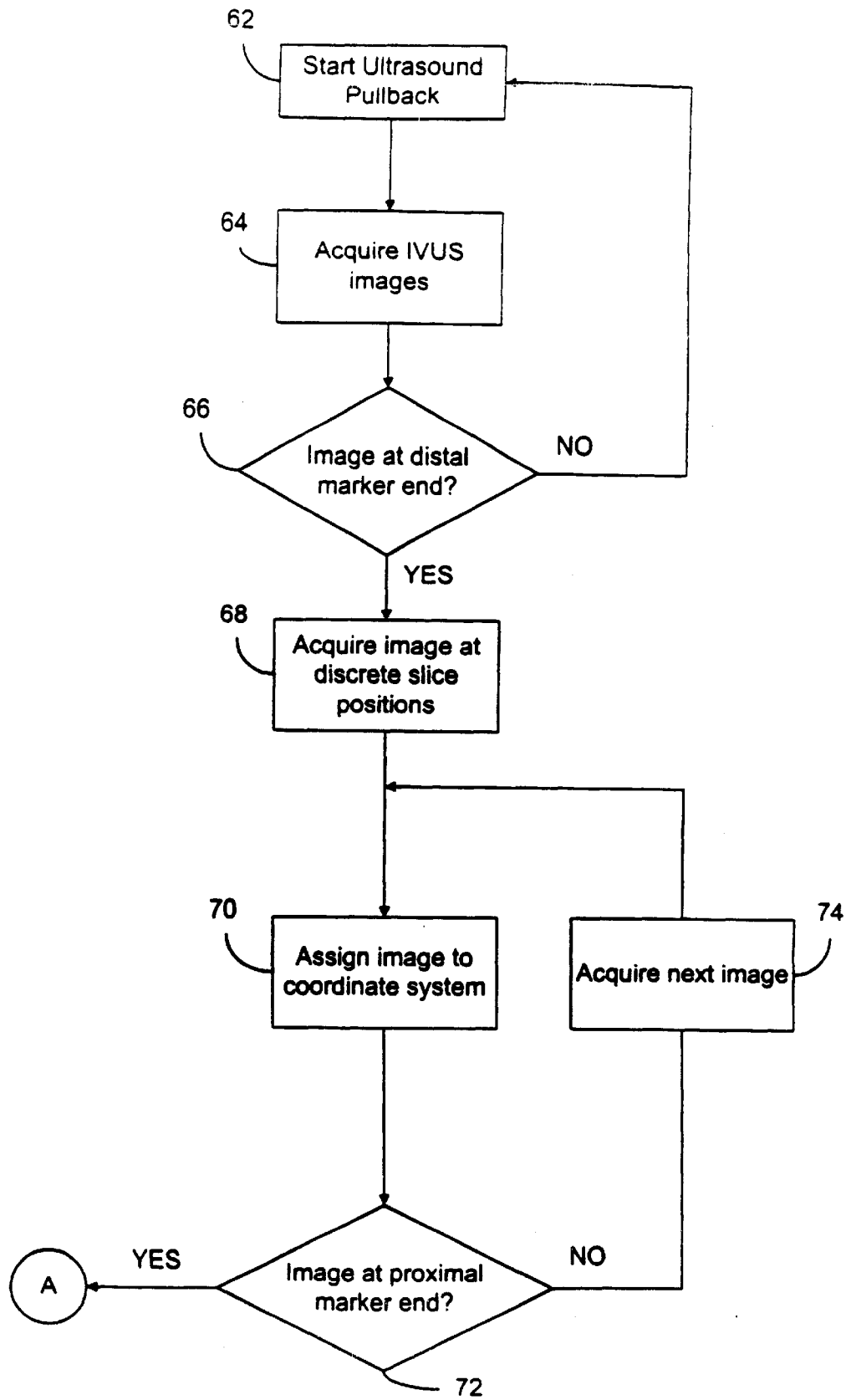
FIGS. 2A and 2B are flow charts of a method for determining the optimal dosimetry according to a preferred embodiment of the invention.
Figure 2B:
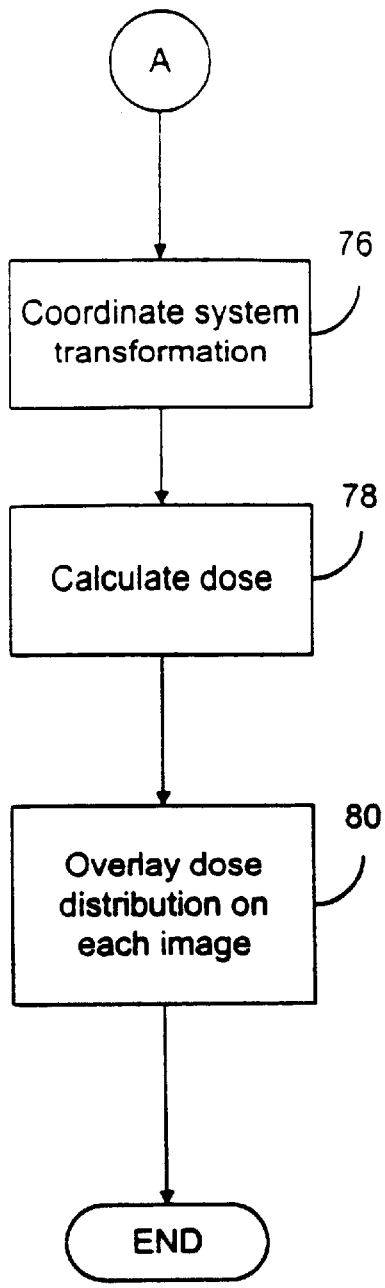

A method for calculating and registering dose with ultrasound images will be described with reference to FIGS. 2A and 2B. At step 62, the ultrasound transducer 14 is inserted within the blood vessel or other tissue to be treated. At a step 64, the imaging system 12 acquires a transverse image at the position of the transducer 14 and determines, at step 66, whether the image is at a distal marker end. A distal end of the treatment volume may be indicated by a marker band at an end on a receptacle for the ultrasound transducer 14 which is visible on images displayed on the imaging system 12. With the marker bands, the proximal and distal ends of a treatment path may be used to define the treatment volume. Alternatively, the proximal and distal ends of the treatment volume may be defined by imaging anatomical landmarks or by viewing the position of the transducer 14 at the beginning of the treatment volume by some external device, such as fluoroscopy, diagnostic x-rays, CT, or MRI scans. The length along the treatment volume may therefore be determined from information generated by the automatic pull-back transducer 14 of imaging system 12 or by calibrated measurements on the external device.

The transducer 14 is moved along the length of the blood vessel or tissue to be treated until the transducer 14 is at a distal end of the treatment volume. At step 68, the imaging system 12 acquires an image at a discrete transverse slice through the blood vessel. The imaging system 12 assigns the image to a coordinate system at step 70 and determines, at step 72, whether the present image is at the proximal marker end. If the image is not at the proximal marker end, then at step 74 the imaging system 12 acquires the next image at the next position along the length of the treatment volume and at step 70 assigns this image to the established imaging coordinate system. In this manner, transverse images along the entire length of the treatment volume are acquired and assigned to the imaging coordinate system.

After images have been acquired for each position along the treatment volume, the treatment planner 20 receives the dose prescription 28 and the dose calculator 30 calculates the desired dose at step 76. The dose is calculated such that each radiation source has an independent coordinate system describing its location within the blood vessel. Each image acquired with the imaging system 12 in contrast, is placed on a Cartesian coordinate system with each pixel having a unique x and y coordinate value and each axial image having a unique z coordinate based on its distance from the distal end of the treatment volume. At step 78, a coordinate system transformation is executed by the dose and image registration unit 34 so that the image coordinate system may be registered with the radiation source coordinate system. In order to register the images and radiation source, internal landmarks are identified for establishing the location and position of the radiation source with respect to the imaging system 12. These landmarks are visible from an imaging device, such as fluoroscopy and intravascular ultrasound. As discussed above the landmarks may comprise metal marker bands at proximal and distal ends with these bands being placed on the transducer 14. The invention is not limited to the use of these metal marker bands and the landmarks may be identified in other ways, such as with a metal prosthesis, through identification of internal branching arteries, or through other ultrasonically visible marks that appear as an artifact on the image.

At step 80, the dose and image registration unit 34 overlays the dose distribution on each image of the treatment volume. The dose and image registration unit 34 at step 80 furthermore provides the superimposition of dose and images to the monitor 40 or other output device, such as the video recorder 38. In this manner, visualization of isodose distributions on each image or reformatted image occurs immediately and this information may be used to optimize subsequent therapy. At step 82, these images are evaluated to optimize subsequent therapy.

Figure 3A:
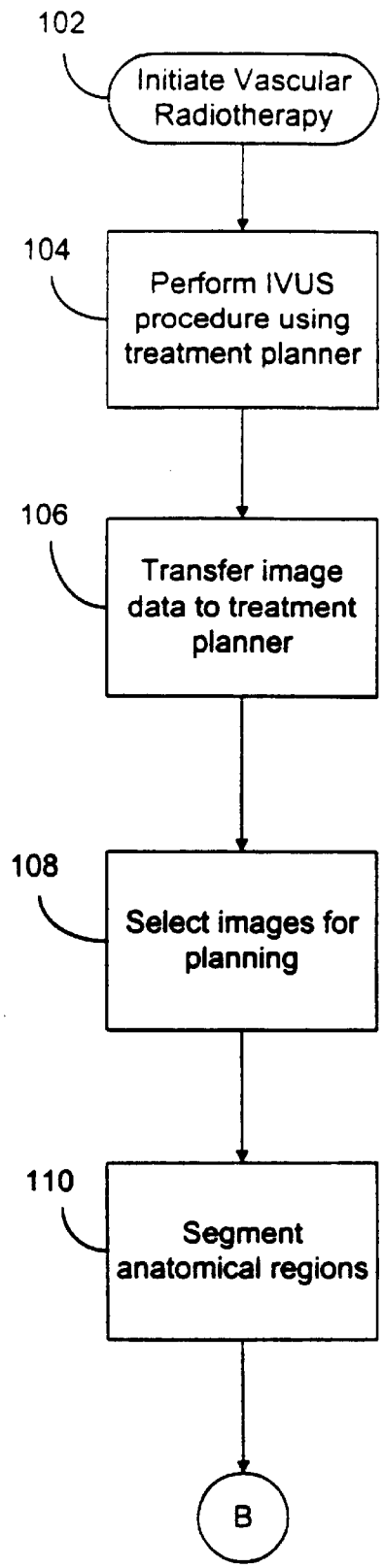
FIGS. 3A to 3C are flow charts of a method for obtaining a treatment plan according to a preferred embodiment of the invention.
Figure 3B:
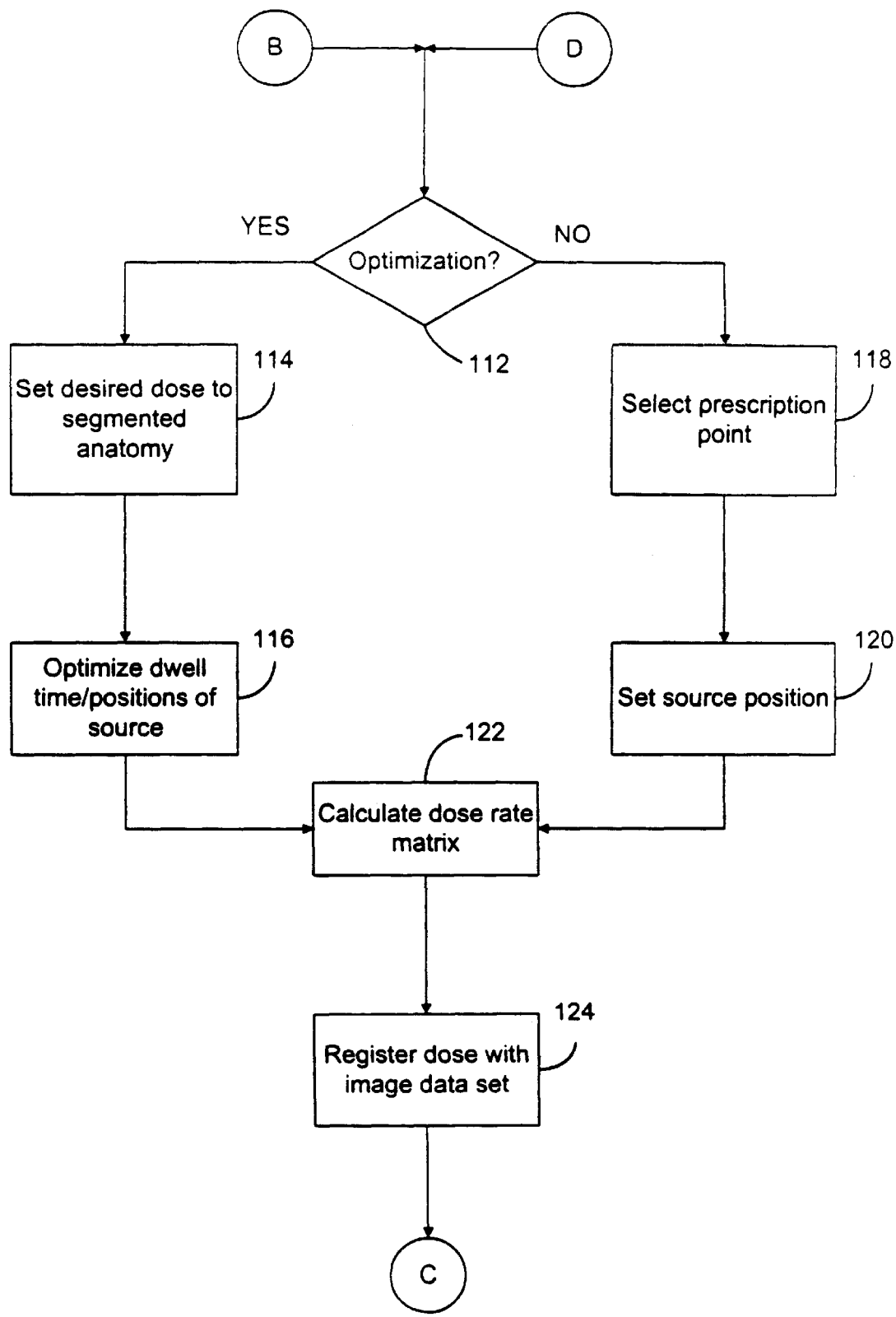
Figure 3C:
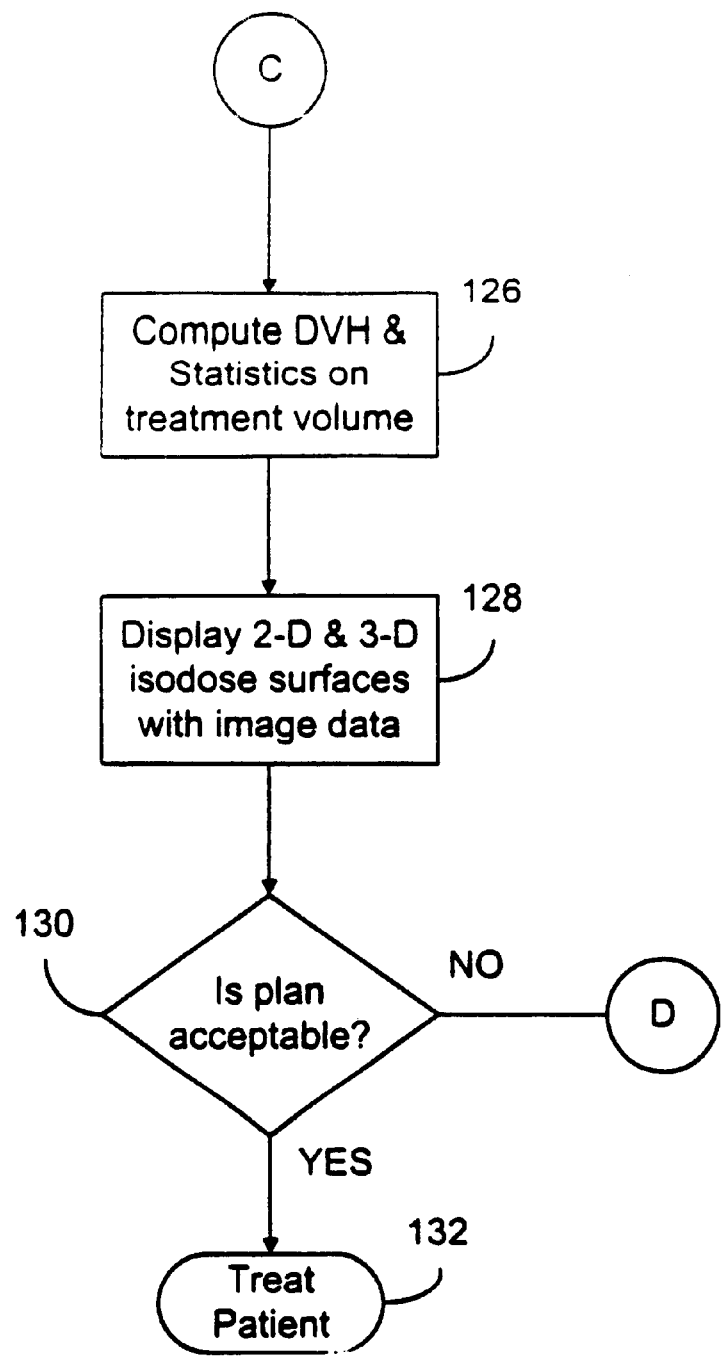

A method for performing vascular radio therapy to arrive at an optimal treatment plan will now be described with reference to FIGS. 3A to 3C. Vascular radio therapy is initiated at step 102 and at step 104 intravascular ultrasound is performed with the imaging system 12 using automated pullback. At step 106 the images acquired from the imaging system 12 are transferred to the treatment planner, as described in FIGS. 2A and 2B, at step 108 the treatment planner 20 selects those images within the treatment volume, and at step 110 the treatment planner 20 segments anatomical regions or an automated segmentation method may be used.

At step 112, an inquiry is made at the treatment planner 20 as to whether computer-aided optimization should be performed. If optimization should be performed, then at step 114 the optimizer 32 sets the desired dose to the segmented anatomy and at step 116 the dwell time and positions of the radiation source or sources are optimized. Any suitable optimization method may be used, such as the Simplex method or other linear programming, least squares, or simulated annealing. At step 122, the dose rate matrix is then calculated. If optimization is not to be performed, then at step 118 a prescription point is selected and at step 120 a source position is set. The treatment planner 20 then calculates the dose rate matrix based upon the selected prescription point and set source position. At step 124, the dose and image registration unit 34 registers the dose with image data.

At step 126, the treatment planner 20 computes DVH and statistics for display on monitor 40. At step 128, 2-D and 3-D superimposed isodose surfaces with imaging data are calculated and displayed on the monitor 40. Next, at step 130, a clinician determines whether the treatment plan is acceptable. If the plan is not acceptable, then processing returns to step 112 for another iteration of optimization or for the selection of different prescription points or source positions. When the treatment plan is acceptable, processing terminates at step 132 and the patient is treated.

Figure 4:
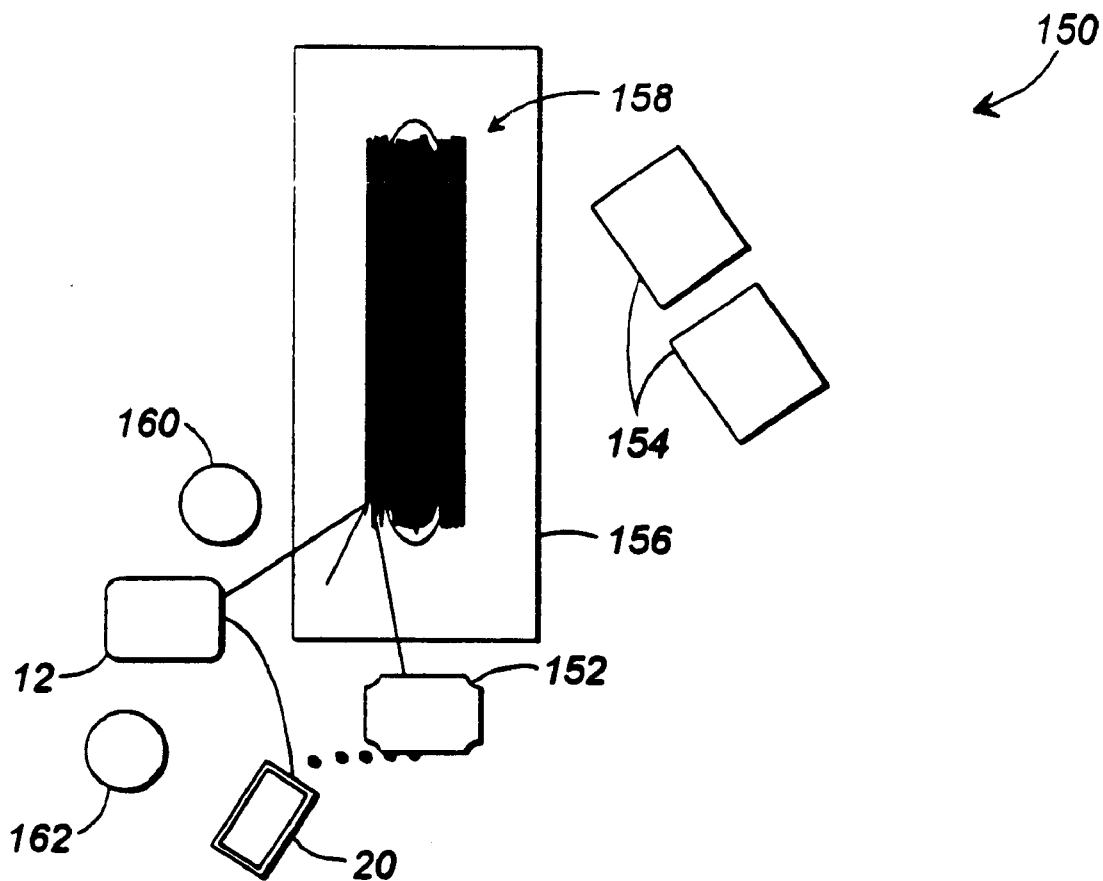
FIG. 4 is an exemplary operating room layout incorporating the system of FIG. 1.

An example of a layout of the imaging system 12 and treatment planner 20 for vascular radiotherapy is shown is FIG. 4. As shown in the layout 150, a patient 158 is placed upon an operating table 156 and monitors 154 for fluoroscopy are placed to one side. A cardiologist or interventional radiologist 160 is positioned near the patient 158 and controls the positioning of the ultrasound transducer 14 and other catheters. A radiation delivery device 152 is positioned near the treatment planner 20, which is also in close proximity to the imaging system 12. A radiation oncologist 162 is advantageously positioned proximate the imaging system 12 and treatment planner 20.

The voice recognition unit 34 of the treatment planner 20 allows the physician administering the treatment, who is dressed in sterile garb, to provide verbal commands to the treatment planner 20 in order to control operations of the treatment planner 20. The treatment planner 20 allows the patient 158 to remain at one location while the dose is calculated and while the optimal treatment plan is derived. The voice recognition unit uses a command and control engine for converting speech to text. One engine commercially available is the Microsoft Speech Engine. This engine can be used to incorporate voice commands for controlling software operations.

Figure 5:
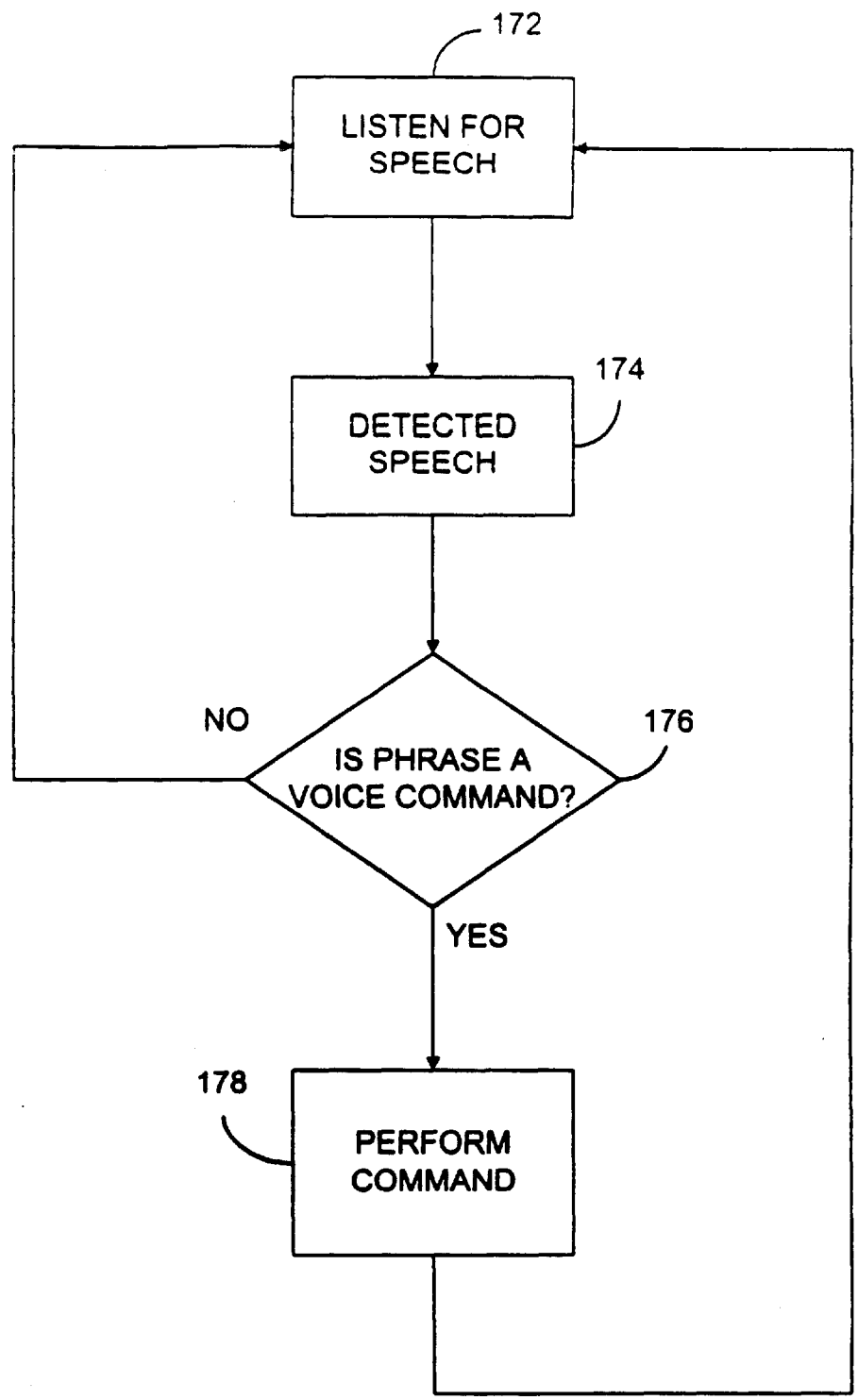
FIG. 5 is a flow chart illustrating a method of operation for a voice recognition unit of FIG. 1.

FIG. 5 shows a general method of operation for the speech voice recognition unit 34. At step 172, the voice recognition unit 34 listens for speech and detects speech at step 174. At step 176, the voice recognition unit 34 determines whether the phrase detected is a verbal command. If the speech is a verbal command, then at step 178 the voice and recognition unit 34 performs the command and returns to step 172 in order to continue to listen for speech. If the detected speech is not a command, as determined at step 176, then the voice recognition unit 34 returns directly to step 172 and listens for speech.

Because the imaging is performed within the cath lab, the patient 158 need not be moved subsequent to derivation of the treatment plan but rather remains at the same location for the actual surgical procedure. Because the imaging system 12 and treatment planner 20 remain within the surgical area, the imaging system 12 and treatment planner 20 may be used during a procedure to alter the treatment plan in the event that an unforeseen circumstance arises.

The imaging system 12 and treatment planner 20 provide a number of advantages over conventional treatment methods. For instance, whereas conventional techniques measure distances from a radiation source to a treated surface via an external device, the invention uses an intravascular ultrasound system 12 to acquire in-vivo images at the position of the radiation source. In other words, the ultrasound transducer 14 is placed at the position of the radiation source thereby allowing extremely accurate measurements to be obtained. The images obtained from the imaging system 12, furthermore, are not limited to two-dimensional images which have inherent inaccuracies due to variations in the third dimension but instead has the treatment planner 20 for formulating three-dimensional images of the treatment volume.

Figure 6A:
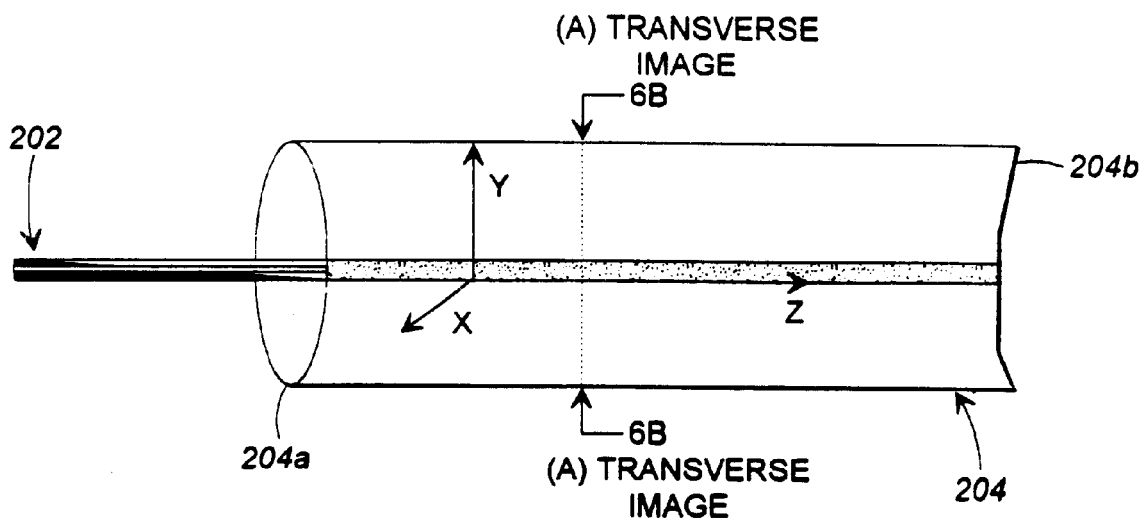
FIG. 6A is a perspective view of a guide catheter and FIG. 6B is an exemplary ultrasound image.
Figure 6B:
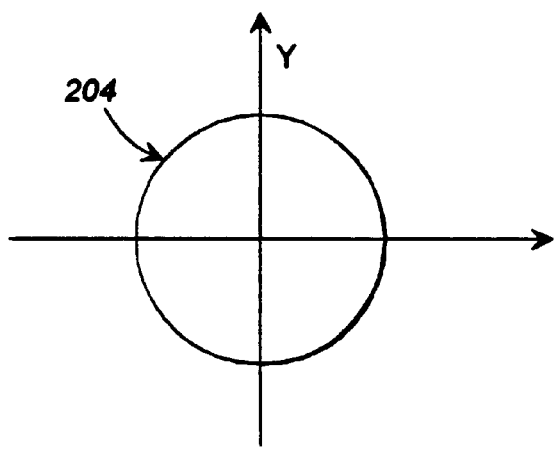

The step 76 of transforming between the IVUS coordinate system and radiation source coordinate system will be described in more detail with reference to FIGS. 6A and 6B. FIG. 6A is a side view of an ultrasound imaging wire 202 and FIG. 6B is a transverse ultrasound image. FIGS. 6A and 6B illustrate the imaging coordinate system 12 associated with the ultrasound imaging wire 202 inside a guide catheter 204 and vessel anatomy used by the treatment planner 20. The z-axis is directed from a distal end 204a to proximal end 204b along the direction of the guide catheter 203. An image plane is generally normal to the axial direction of the catheter 202 and establishes the z coordinate of the transverse ultrasound image. The x-y plane contains the coordinates associated with the axial direction of the catheter 202 on ultrasound image plane. This coordinate system defined by the x, y, and z axes is referred to as the IVUS coordinate system.

The radiation source is defined in the IVUS coordinate system and the longitudinal axis of the radiation source is parallel with the z-axis of the IVUS coordinate system. Each radiation source's center position is assigned a unique set of x, y, and z coordinates in the IVUS coordinate system. The dose calculation points are also defined in the IVUS coordinate system. At step 78, the dose is calculated by the dose calculator 30 from each radioactive source's position in the radiation source coordinate system. In order to calculate the dose to any point in the IVUS coordinate system, a transformation between the IVUS coordinate system and the radiation source coordinate system must be established. To transform a point $(x_I, y_I, z_I)$ from the IVUS coordinate system for the calculation in the radiation source coordinate system $(x, y, z)$, the following equation is used:

$$\begin{bmatrix} x \\ y \\ z \\ 1 \end{bmatrix} = \begin{bmatrix} 1 & 0 & 0 & t_x \\ 0 & 1 & 0 & t_y \\ 0 & 0 & 1 & t_z \\ 0 & 0 & 0 & 1 \end{bmatrix} \begin{bmatrix} x_1 \\ y_1 \\ z_1 \\ 1 \end{bmatrix}$$

where $(t_x, t_y, t_z)$ is the seed center position for the radiation source of interest defined in the IVUS coordinate system.

Figure 7A:
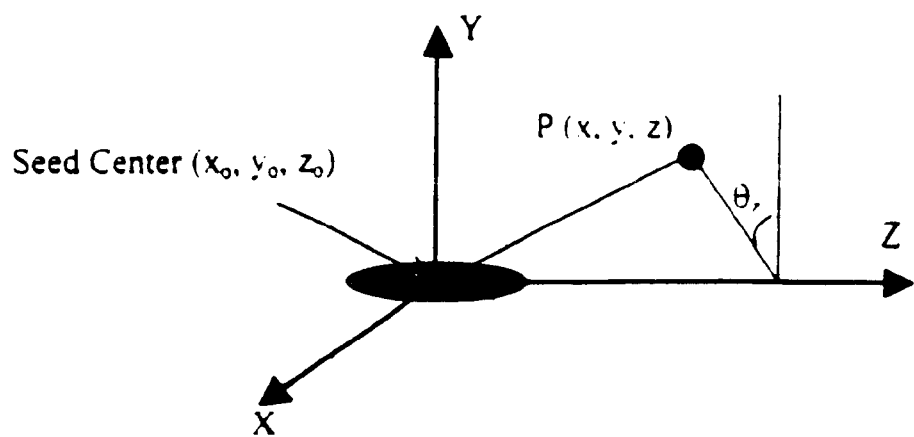
FIGS. 7A and 7B are graphs of coordinate systems for radiation source and for an image acquired of a treatment volume, respectively.

The step 78 of calculating dose to points in the radiation source coordinate system will be described below in more detail. The treatment planner 20 uses more than one dose calculation model depending on the type of radiation source with these models including semi-empirical methods, Monte Carlo methods, and experimentally measured data using a radiation detector with an adequate spatial resolution. A description of the model used for catheter-based radioactive line sources, including seeds, will be provided as an example for step 76. The dose is calculated by the dose calculator 20 within the treatment volume at any 3-D point for a radioactive line source. The dose calculator 20 uses the coordinates of the seed center $(x_o, y_o, z_o)$ and calculates the dose at a point in space, $P(x, y, z)$. The longitudinal axis of the seed or line source is parallel with the z-axis of the coordinate system shown in FIG. 7A. A coordinate system transformation is first performed from $P(x, y, z)$ to $P'(x', y', z')$ located on a y-z plane. To perform this transformation, $P(x, y, z)$ is rotated around z-axis in the clockwise direction by $\theta_z$ to obtain $P'(x', y', z')$, according to the following equation:

$$P' = \begin{bmatrix} \cos\theta_z & \sin\theta_z & 0 \\ -\sin\theta_z & \cos\theta_z & 0 \\ 0 & 0 & 1 \end{bmatrix} \begin{bmatrix} x \\ y \\ z \end{bmatrix}$$

Figure 7B:
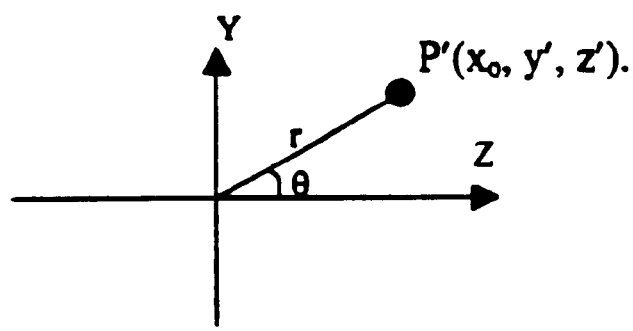

A 2-D coordinate system shown in FIG. 7B is then used for dose calculation with $x=x_0$. The dose calculator 20 next calculates the dose to the point $P'(x_o, y', z')$ and $P'(y', z')$ is transformed to $P''(r, \theta)$ according to the following relationship:

$$r = \sqrt{(y' - y_o)^2 + (z' - z_o)^2}$$

$$\theta = \tan^{-1}\left(\frac{|y_o - y'|}{|z_o - z'|}\right)$$

The American Associate of Physicists in Medicine Task Group 43 ("AAPM TG43") in *"Dosimetry of interstitial brachytherapy sources: Recommendations of the AAPM Radiation Therapy Committee Task Group No. 43,"* Med. Phys. 22 (2), pp. 209–234, February 1995, recommends a dose calculation formalism if the distance r from the source and angle θ is known according to FIG. 7B. The dose calculator 20 preferably calculates the dose to $P''(r, \theta)$ using TG43 experimentally determined factors according to the following relationships:

$$D(x, y, z) = D'(x, y, z) = D''(r, \theta) = (S_d) \cdot g(r) \cdot \frac{G(r, \theta)}{G\left(r_o, \frac{\pi}{2}\right)} \cdot F(r, \theta)$$

This step is performed for each dose calculation point and each seed position. The treatment planner 20 sums the contributions from each source position to each calculation point to provide a composite dose distribution.

Figure 8A:
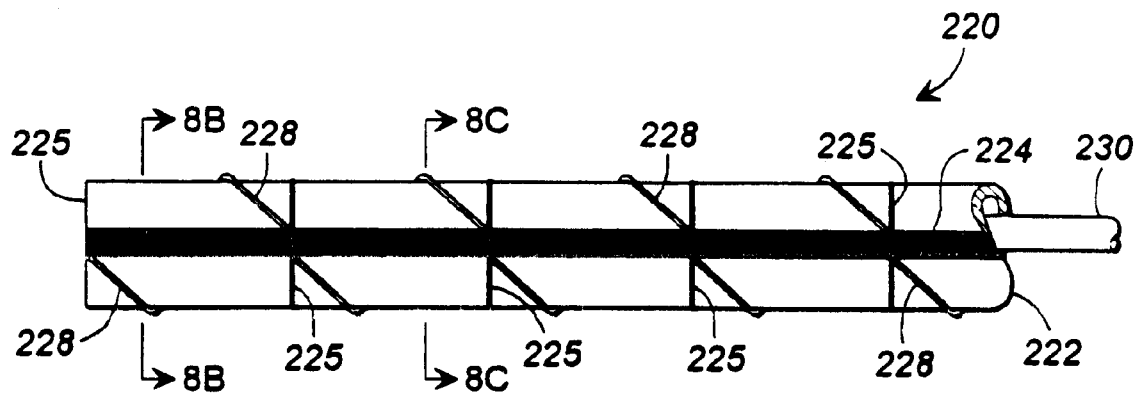
FIG. 8A is a top plan view of a catheter guide according to a preferred embodiment of the invention.
Figure 8B:
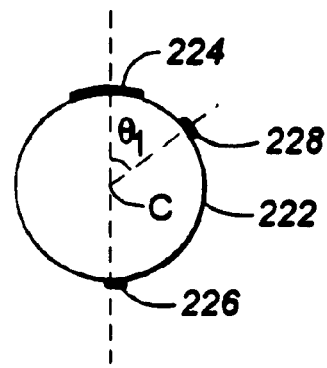
FIGS. 8B and 8C are ultrasound images acquired at two different positions along a length of the catheter guide.
Figure 8C:
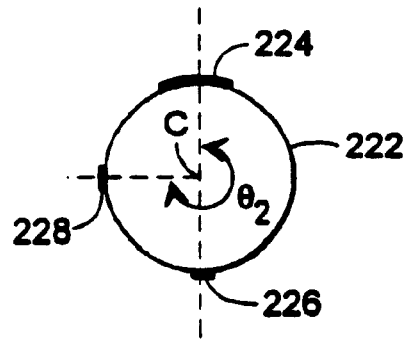

A catheter 220 according to another aspect of the invention is shown in FIGS. 8A to 8C. The catheter 220 is a stereotactic localizing guiding catheter allowing clinicians to precisely determine the position and orientation of the ultrasonic transducer 14. To simplify the illustration of the invention, the ultrasonic transducer 14 has not been depicted in FIGS. 8A to 8C.

The catheter 220 includes a catheter body 222 generally formed in a cylindrical shape having proximal and distal ends. The catheter 220 is provided with a set of markers 224, 226, and 228 which allow clinicians to determine the location and orientation of the ultrasonic transducer 14. The first marker 224 extends along a length of the catheter 220 in parallel to the longitudinal axis of the catheter 220. The second marker 226 also extends along the length of the catheter 220 and is parallel to both the longitudinal axis of the catheter 220 and to the first maker 224. In this example, marker 224 is formed to have a width larger than that of the second marker 226 for reasons that will be apparent from the description below. The third marker 228 is formed along a straight line and wraps around the body 222 of the catheter 220 in a spiral fashion. The catheter 220 may also include one or more 20 regularly spaced markers 225, each of which forms a band around the circumference of the catheter body 222.

As described in greater detail above, one problem with conventional imaging techniques is that it is difficult to determine the precise location and orientation of a catheter within a patient. This difficulty is associated with not only imaging catheters but also with delivery catheters. Catheter 220 according to the invention addresses these problems by allowing clinicians to determine the precise location and orientation of a catheter. Each of the markers 224, 226 228, and 225 produces image artifacts in ultrasound images acquired with the transducer 14. Depending upon the relative positions of the markers 224, 226, 228, and 225, a clinician can determine the position of a catheter along the length of the catheter guide 220.

The manner of determining the precise location and orientation of a catheter within the catheter guide 220 will be described with reference to the examples shown in FIGS. 8B and 8C. FIGS. 8B and 8C illustrate ultrasound images acquired at positions indicated by the arrows 8B and 8C in FIG. 8A, respectively. Each ultrasound image, such as the images shown in FIGS. 8B and 8C, includes image artifacts for image markers 224 and 226. These two markers 224 and 226 are used to provide a reference axis from which an orientation of the catheter may be deduced. The image marker 224 forms an image artifact which is distinct from the image artifact produced by image marker 226. Consequently, clinicians can easily align the image artifacts produced from markers 224 and 226 with, for instance, a z axis extending along a length of a patient. Although a single marker, such as marker 224, may provide a reference point from which clinicians can eslimate a reference axis, the use of two markers 224 and 226 enable clinicians to accurately determine a reference axis and hence accurately determine the orientation of the catheter.

Whereas markers 224 and 226 are used to determine the orientation of a catheter, the markers 225 and 228 are used to determine the position of the catheter along the length of the catheter guide 220. The marker 228 wraps around the catheter body 222 in a regular manner traversing a distance along a length of the catheter body 222 proportionate to the marker's 228 angular position. In this example, the marker 228 extends from one marker 225 to the next marker 225 with the markers 225 being equally spaced from each other, such as every 10 cm. The clinician would therefore view an image artifact produced by an image marker 225 every 10 cm as the transducer 14 is being moved along the catheter guide 220.

To accurately determine the location of the transducer 14 or other catheter between the markers 225, the clinician can calculate the catheter's position based on the angular position of marker 228. The ultrasound image produced by the transducer 14 produces image artifacts for markers 224, 226, and 228 with the artifact for marker 228 being at an angle θ relative to a reference axis extending from marker 224 to marker 226. In general, the distance d of a catheter along the length of the catheter guide 220 is determined according to the following equation:

$$d = \left(\frac{\theta}{360}\right) \cdot L$$

where θ is an angular position of the marker 228 relative to marker 224 and L is the wrapping distance, which in this example is the length between markers 225.

For example, with reference to FIG. 8B, an artifact for image marker 228 is at an angular position of $\theta_1$ where $\theta_1$ is equal to 45 degrees. The distance d of the catheter is therefore determined according to the following equation:

$$d = \left(\frac{45}{360}\right) \cdot 10 \text{ cm} = 1.25 \text{ cm}$$

The clinician can therefore easily determine that the ultrasound image was taken at a distance of 1.25 cm from the previous marker band 225. As another example, when the transducer 14 is at the position 8C along the length of the catheter guide 220, the artifact for marker 228 is at an angle $\theta_2$ where $\theta_2$ is equal to 270 degrees. The position of the transducer 14 at this location is determined according to the following equation:

$$d = \left(\frac{270}{360}\right) \cdot 10 \text{ cm} = 7.50 \text{ cm}$$

The catheter guide 220 eliminates much of the guesswork presently associated with the use of catheters. Rather than estimating the location of the transducer 14 or other catheter using a pull-back mechanism, the precise location of the catheter may be determined from artifacts produced from markers 224, 228 and 225. The ability to accurate locate a catheter provides clinicians with numerous advantages, such as the ability to accurately determine the location of a lesion, the ability to accurately deliver radiation to the precise location of the lesion, and the ability to acquire follow-up images precisely at the location of the lesion in order to assess the effectiveness of the treatment. Through the use of artifacts produced by markers 224 and 226, clinicians can accurately determine the precise orientation of a catheter. As a result, clinicians may accurately control the delivery of radiation to only certain angular segments of an artery thereby avoiding the delivery of radiation to healthy tissue. Furthermore, by imaging the treatment volume simultaneously with delivering radiation, clinicians can ensure that the correct dosage of radiation is delivered to the treatment volume.

The catheter body 222 may be comprised of any suitable material usually formed from any one of a wide variety of biologically compatible materials, typically being made from natural or synthetic polymers, such as silicone, rubber, natural rubber, polyethylene, polyvinylchloride, polyurethanes, polyesters, polytetrafluoroethylenes (PTFE). The catheter body 222 is often formed as a composite having a reinforcement material incorporated within the polymeric body in order to enhance its strength, flexibility, and toughness. Suitable enforcement layers include but are not limited to wire mesh layers. The flexible tubular members of the catheter body 222 will normally be formed by extrusion with one or more integral lumens being provided. If desired, a diameter the catheter can be modified by heat expansion and shrinkage using conventional techniques. The techniques for forming vascular catheters are well known to those skilled in the art.

The overall dimensions of the catheter 220 will depend on the particular application of the catheter, with the length varying widely but typically between about 40 cm and 150 cm and usually being between about 40 cm and 120 cm, for peripheral catheters and being between about 110 cm and 150 cm for coronary catheters. The diameter of the catheter body 222 may also valy widely, with the diameter typically being between about 3 to 6 French (F), wherein one French equals 0.33 mm.

The markers 224, 226, 228, and 225 may be applied to the catheter body 222 by any suitable technique, including conventional techniques used for forming fluoroscopic rings on intravascular catheters. A wide variety of ultrasonically visible marks can be provided including a hole formed in the body 222, an ultrasonically opaque material secured on or in the body 222 (such as paint, a flat piece of metal ribbon, or other low profile material capable of reflecting acoustic energy), or other ultrasound absorbing material such as urethanes, silicone, epoxies. The markers 224, 226, 228, and 225 may be formed using a heavy metal foil, such as gold or platinum, bonded to the exterior of the catheter body 222 using heat or a suitable adhesive, typically by embedding the foil into the catheter body 222 using heat. The markers are preferably encapsulated within a thin sheath, typically by heat shrinking polyethylene or other suitable thermoplastic, over the exterior of the catheter body 222.

The forgoing description of the preferred embodiments of the invention has been presented only for the purpose of illustration and description and is not intended to be exhaustive or to limit the invention to the precise form disclosed. Many modifications and variations are possible in light of the above teaching.

For example, although the invention has been described with the prevention of restenosis within a blood vessel, the invention may be used to treat other tissues. Moreover, the invention is not limited to the prevention of restenosis but may used to accurately deliver a dose of radiation for reasons other than the prevention of restenosis. The invention, for instance, may be used in the delivery of radiation to cancerous tissues, such as cervical cancer.

Additionally, the invention has been described with reference to an imaging transducer 14 and a separate radiation delivery catheter. It should be understood that the imaging transducer 14 and the radiation catheter may be combined into a single unit.

Further, the catheter guide according to the invention may be formed with any number of markers 225 or may be formed without markers 225. Additionally, although the markers 224 and 226 are distinguishable based on their widths, the markers 224 and 226 may be distinguishable in other ways. For instance, markers 224 and 226 may be formed at different heights or markers 224 and 226 may be formed with different materials resulting in different image artifacts. As should be apparent to those skilled in the art, maker 228 may wrap entirely around the body 222 or may only partially wrap around the body 222. The angle at which the marker 228 wraps around the body 222 may also be varied in order to establish a desired relationship between the angular difference $\theta$ and the length L. For instance, for an angular difference of 90 degrees, the marker 228 may traverse 1 cm, 5 cm, 10 cm or any desired distance along the length of the body 222. As another example, marker 224 may be formed as a band of two markers while marker 226 remains a single marker. Also, although the catheter guide 220 has been described with reference to the ultrasound transducer 14, the catheter guide 220 may be designed to operate with other types of imaging transducers.

The guide according to the invention is not restricted to catheters used to treat restenosis may be used with any suitable device and for any suitable purpose. Thus, the guide may be used for diagnosis, treatment, or verification. The guide, moreover, may be used with an endobronclial catheter, an intra-uterine device, with metal cylinders which are either straight or curved, or with other interstitial or intra-cavity devices. Other uses of the guide will become apparent to those skilled in the art.

The guide according to the invention is furthermore not limited to use with ultrasound imaging transducers but may be used with other imaging techniques. The guide, for instance, may be used with magnetic resonance (MR), computer tomographic (CT), or other tomographic techniques.

The embodiments were chosen and described in order to explain the principles of the invention and their practical application so as to enable others skilled in the art to utilize the invention and various embodiments and with various modifications as are suited to the particular use contemplated.

What is claimed is:

1. A guide, comprising:

a body having a longitudinal axis and having a distal end and a proximal end;

a first marker extending along the body in parallel to the longitudinal axis; and a second marker extending along the body in parallel to the longitudinal axis and in parallel to the first marker, the second marker being placed on the body at a predetermined location relative to the first marker;

wherein the first and second markers produce artifacts in an image generated with an imaging device and wherein clinicians can determine an orientation of the image from the relative positions of the artifacts from the first and second markers.

2. The guide as set forth in claim 1, wherein the first and second markers are located opposite each other along a line extending through a center of the body.

3. The guide as set forth in claim 1, wherein the image artifact produced by the first marker is distinct from the image artifact produced by the second marker.

4. The guide as set forth in claim 1, wherein the imaging device comprises an ultrasound transducer and wherein the first and second markers produce image artifacts in ultrasound images.

5. The guide as set forth in claim 1, wherein the first and second markers have different widths.

6. The guide as set forth in claim 1, further comprising a third marker having an angular position on the body which varies along the length of the body.

7. The guide as set forth in claim 6, wherein the third marker produces an image artifact from which clinicians can determine the location of the image along the guide.

8. The guide as set forth in claim 1, wherein the guide is for receiving a catheter.

9. The guide as set forth in claim 1, wherein the guide is for receiving an intracavity device.

10. The guide as set forth in claim 1, wherein the guide is for receiving an interstitial device.

11. The guide as set forth in claim 1, wherein the guide is for receiving the imaging device.

12. A guide, comprising:

a body having a longitudinal axis and having a distal end and a proximal end;

a first marker extending along the body in parallel to the longitudinal axis; and a second marker placed on the body and having an angular position on the body which varies along the length of the body;

wherein a portion of the body contains the first and second markers and the first and second markers intersect within this portion, wherein the first and second markers produce artifacts in an image generated with an imaging device and wherein clinicians can determine a position of an imaging transducer along the guide from the relative positions of the artifacts from the first and second markers.

13. The guide as set forth in claim 12, wherein the image artifact produced by the first marker is distinct from the image artifact produced by the second marker.

14. The guide as set forth in claim 12, wherein the imaging device comprises an ultrasound transducer and wherein the first and second markers produce image artifacts in ultrasound images.

15. The guide as set forth in claim 12, further comprising a third marker extending around a periphery of the body wherein the first and second markers have different widths.

16. The guide as set forth in claim 12, wherein the guide is for receiving a catheter.

17. The guide as set forth in claim 12, wherein the guide is for receiving an intracavity device.

18. The guide as set forth in claim 12, wherein the guide is for receiving an interstitial device.

19. The guide as set forth in claim 12, wherein the guide is for receiving the imaging device.

* * * * *